(12) United States Patent
Vom et al.

(10) Patent No.: US 9,733,166 B2
(45) Date of Patent: Aug. 15, 2017

(54) DEVICE AND METHOD FOR TISSUE HANDLING AND EMBEDDING

(75) Inventors: Eduardo Vom, Brunswick East (AU); Chester John Henderson, Preston (AU); Craig Matthew Lewis, Glen Iris (AU)

(73) Assignee: LEICA BIOSYSTEMS MELBOURNE PTY LTD, Mount Waverly Victoria (AU)

( * ) Notice: Subject to any disclaimer, the term of this patent is extended or adjusted under 35 U.S.C. 154(b) by 2184 days.

(21) Appl. No.: 12/520,018

(22) PCT Filed: Dec. 18, 2007

(86) PCT No.: PCT/AU2007/001959
§ 371 (c)(1),
(2), (4) Date: Jan. 21, 2010

(87) PCT Pub. No.: WO2008/074073
PCT Pub. Date: Jun. 26, 2008

(65) Prior Publication Data
US 2010/0151513 A1 Jun. 17, 2010

Related U.S. Application Data

(60) Provisional application No. 60/870,744, filed on Dec. 19, 2006.

(30) Foreign Application Priority Data

Dec. 18, 2006 (AU) .................................. 2006907016

(51) Int. Cl.
*G01N 1/36* (2006.01)

(52) U.S. Cl.
CPC ....................................... *G01N 1/36* (2013.01)

(58) Field of Classification Search
CPC ........................................................ G01N 1/36
USPC ........................................... 436/176; 422/102
See application file for complete search history.

(56) References Cited

U.S. PATENT DOCUMENTS

| | | | |
|---|---|---|---|
| 3,982,862 A | 9/1976 | Pickett et al. | |
| 4,801,553 A * | 1/1989 | Owen et al. | 436/174 |
| 5,843,700 A | 12/1998 | Kerrod et al. | |
| 7,514,042 B2 * | 4/2009 | Lihl et al. | 422/536 |
| 2003/0119200 A1 * | 6/2003 | Taft | G01N 1/36 436/176 |
| 2005/0226770 A1 * | 10/2005 | Allen et al. | 422/63 |

FOREIGN PATENT DOCUMENTS

| | | |
|---|---|---|
| WO | 00/19897 A1 | 4/2000 |
| WO | 01/44784 A1 | 6/2001 |

OTHER PUBLICATIONS

European Search Report Dated May 17, 2013, issued in counterpart European Patent Application No. 07845400.6.

* cited by examiner

*Primary Examiner* — Ann Lam
(74) *Attorney, Agent, or Firm* — Sughrue Mion, PLLC

(57) ABSTRACT

A tissue embedder comprising a transport mechanism for an input member, the input member adapted to hold a plurality of tissue supports, with each tissue support associated with a mould, a wax bath and a cooling station wherein the transport mechanism moves the input member from a wax bath to a cooling station.

12 Claims, 12 Drawing Sheets

Figure 10: Flowchart of a method according to an embodiment of the present invention:

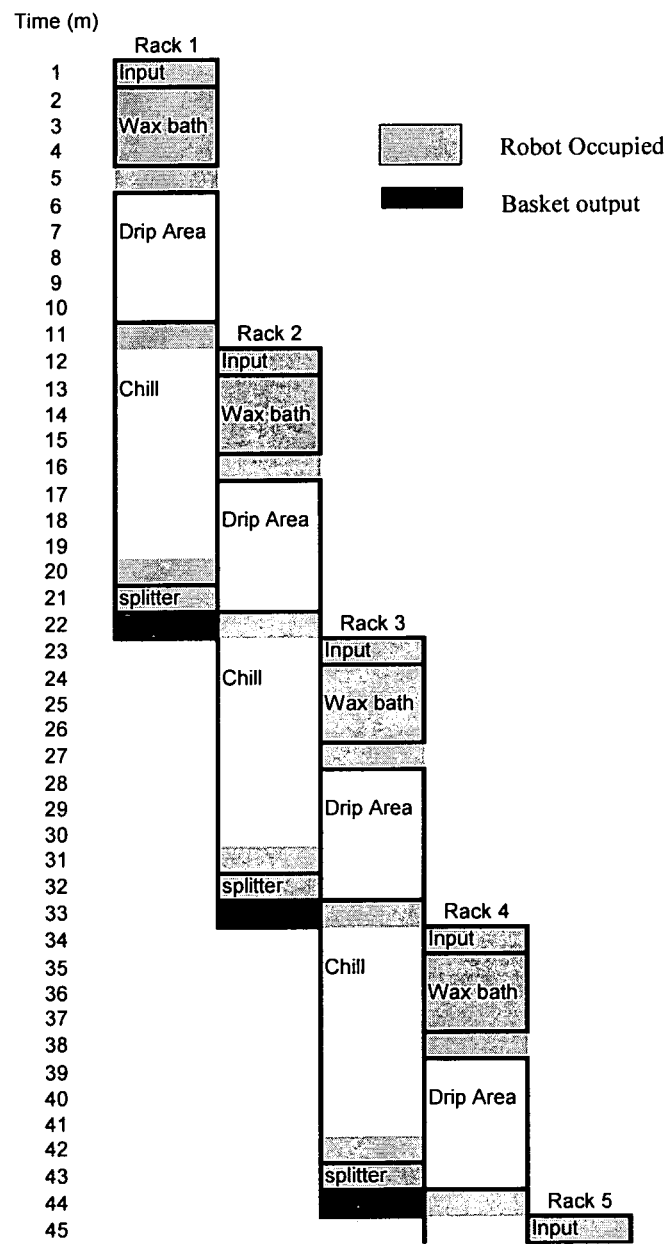
Figure 16: Continuous workflow according to one embodiment

DEVICE AND METHOD FOR TISSUE HANDLING AND EMBEDDING

RELATED APPLICATIONS

This application claims priority from AU2006907016 and U.S. 60/870,744, the contents of which are incorporated herein in entirety by reference.

FIELD OF INVENTION

The present invention relates to a device and method for handling and embedding tissue samples. In particular, the present invention relates to a device and method for automated embedding of tissue samples for histological analysis.

BACKGROUND

Rapid and high quality preparation of samples within a histology laboratory, such as tissue sections on a microscope slide, is vital to correctly providing accurate analysis and diagnosis to a patient.

Typically, the workflow within a histology laboratory is as follows:

A biopsy sample is delivered in a container by courier from a doctor's surgery. The sample container is given an accession ID relevant to the laboratory, and is then passed on to the cut-up (grossing) area. Here, the sample is removed from the container, and cut up to excise sections of interest. The sections of interest are placed into one or more tissue cassettes, wherein the tissue specimen is held loosely in a cassette to segregate it from other samples. Each cassette is labelled so the tissue can be identified through the entire process. Various sized cassettes are available, and the choice of cassette will usually depend on the size of the tissue sample. The next step requires the tissue specimen to be processed in a device such as a Leica ASP300. In such a processing, the tissue is dehydrated using alcohol, and then infiltrated with paraffin wax, to form a chemically stable block. Once stabilised and infiltrated with wax, the tissue is then taken from the cassette and oriented into a position appropriate for sectioning.

The orienting step is done manually and requires skilled operators and it can be time consuming to ensure that the tissue specimen is positioned correctly. This step typically involves taking the specimen out of the cassette, selecting the correct size mould to use, dispensing a small volume of wax to the bottom of the mould, and carefully orientating the tissue specimen. It is critical that the specimen is accurately positioned, as the sectioning of the specimen must be in an appropriate plane to reveal the desired cells. The cassette fixture (holding fixture for the microtome) is then placed on the top of the mould, additional wax is dispensed to embed the fixture to the block and the paraffin block then cooled wherein the wax solidifies. The block is then removed from the mould and ready to be mounted on the microtome to be sectioned. The process, from the time a tissue sample arrives in the laboratory, to the point where a block is mounted on the microtome, adds significant delays to the provision of a diagnosis based on the tissue sample.

In order to decrease the time this process takes, several steps have been automated to various extents. However, other steps, such as the embedding process have remained manual or semi automatic in a large number of laboratories. The manual embedding process is typically a slow process with an average of 40-60 samples per hour, and has also proven to be very labour intensive requiring the histotechnician to spend a large proportion of time handling individual cassettes. The repetitive nature of this task also exposes histotechnicians to the risk of RSI injuries. Furthermore, as the process involves many manual steps, there is increased risk of errors occurring. Automation of processes in a histology laboratory is seen as beneficial to reducing turn around time, and can be assisted by automatic embedding.

There remains a need for improved methods and devices for automating the embedding process. The present invention is directed to overcoming or at least alleviating the problems associated with the prior art.

SUMMARY

In a first aspect, the present invention provides a tissue embedder comprising:

a transport mechanism for an input member, the input member adapted to hold a plurality of tissue supports, with each tissue support associated with a mould; a wax bath; a cooling station; wherein the transport mechanism moves the input member from a wax bath to a cooling station.

In a second aspect, the present invention provides a method of embedding multiple tissue supports comprising the steps of:

Placing a plurality of tissue supports in an input member, each tissue support associated with a mould; placing the input member into a wax bath; removing the input member from the wax bath and transporting the input member to a cooling station, to solidify the wax in the moulds.

In one embodiment, the mould is attached to each tissue support prior to the tissue supports being placed into the input member.

In one embodiment, the method according to the second aspect includes the step of, after removing the input member from the wax bath, removing excess wax from the tissue supports.

In one embodiment, the input member is moved to a wax removal station to remove excess wax.

In one embodiment, the method further includes the step of orienting the tissue supports in the input member at an angle from horizontal, to cause wax on the outside of the tissue supports to drain from the supports.

In a third aspect, the present invention provides a method of determining whether to process an input member holding tissue supports including the steps of: locating one or more input members in an input member input region adapted to hold one or more input members; monitoring the level of wax in a wax bath; calculating the amount of wax required to process an input member; only processing an input member if there is sufficient wax in the wax bath to embed all the tissue supports.

In one embodiment, the method according to the third aspect includes the steps of: determining when the wax volume has dropped below a first predetermined level; instructing a wax supply to supply more wax to the wax bath; instructing a wax supply to stop supplying wax to the wax bath when the wax volume exceeds a second predetermined level.

In one embodiment, the method comprises the additional step of: once receiving an instruction to supply more wax, a heater is engaged to melt solid wax, where molten wax is added to the wax bath.

In another embodiment, the method includes the step of: determining when the wax level falls below a third predetermined level, and if the wax volume is below the predetermined level; preventing any further input members from being placed into the wax bath.

In a fourth aspect, the present invention provides a method of embedding tissue supports each containing oriented and processed tissue, including the steps of: placing a plurality of tissue supports into an input member such that each tissue support is oriented in the same direction and each is associated with a mould; placing the input member into a wax bath to a depth to fill all the moulds of the tissue supports in the input member; removing the input member from the wax bath; placing the input member into a cooling region to solidify the wax in each mould.

In one embodiment, the method according to the fourth aspect includes the step of: applying a method of removing trapped air from the tissue supports and moulds in the input member during placement of the input member into the wax bath and/or while the input member is in the wax bath.

In one embodiment, the method includes the step of shaking the input member to remove trapped air.

In one embodiment, the method includes the step of tilting the input member to allow trapped air to escape from the tissue supports within the input member.

In one embodiment, the method includes the step of, prior to placing the input member in a cooling region, shaking and/or tilting the tissue supports in the support holder to remove excess wax on the tissue supports and/or input members.

In a fifth aspect, the present invention provides a method of separating tissue supports from moulds in a input member including the steps of: cooling the wax in the tissue supports and mould to a temperature of below 14 degrees Celsius; supplying force to split one or more of the supports from their respective moulds.

In one embodiment, the method includes the step of maintaining the temperature range in a cooling region of between 4 and 8 degrees Celsius.

In one embodiment, the method includes the step of: cooling the wax to a temperature below 12 degrees Celsius.

In a sixth aspect, the present invention provides an automated device for embedding multiple tissue supports, the device comprising: a transfer assembly operative to transport an input member to a reservoir, wherein the input member is configured to secure a plurality of tissue supports in a substantially tiered arrangement, and the reservoir is configured to contain embedding media and receive the input member.

In one embodiment, the device further comprises a cooling member.

In a seventh aspect, the present invention provides a method for automated embedding of multiple tissue supports, the method comprising:

securing the multiple tissue supports in an input member, wherein the input member is configured to secure the multiple tissue supports in a substantially tiered arrangement; transporting the input member via a transfer assembly to a reservoir containing embedding media.

In one embodiment the method provides continuous throughput of input members.

In an eighth aspect, the present invention provides an apparatus for embedding multiple tissue samples comprising: an embedding chamber holding embedding material and adapted to receive multiple tissue supports; a cooling chamber for cooling multiple tissue supports; a separating mechanism for separating multiple tissue supports from an input member holding multiple tissue supports.

In one embodiment, the cooling chamber comprises: a first region for cooling the tissue supports and input member slowly; and a second region for cooling the tissue supports to a temperature below ambient.

In one embodiment, the first region allows excess embedding material to drip off the input member before solidification of the embedding material.

BRIEF DESCRIPTION OF THE DRAWINGS

FIG. 16 shows a timeline of operations of an embodiment of the present invention.

DETAILED DESCRIPTION OF PREFERRED EMBODIMENTS

Preferred embodiments of the present invention and their advantages may be understood by referring to FIGS. 1-16, like numerals being used for like corresponding parts in the various drawings.

The device and method described hereafter are preferred embodiments only, and the present invention is not limited to these preferred embodiments. The arrangement of elements of the device and method in FIGS. 1-12 in no way limits the present invention. It is within the contemplation of the present invention to arrange or modify elements of the device and method in accordance with other design requirements, such as, the amount of space available to accomplish the device and method of this invention.

As used herein, the term "tissue sample" refers to an orientable tissue sample such as human, animal or plant tissue that is typically made up of a collection of biological cells and includes, but is not limited to, for example, biopsy samples, autopsy samples, surgical samples, cell smears, cell concentrates and cultured cells, and preparations made from micro-organisms. The tissue sample generally includes any material for which microscopic examination of samples of the material prepared on microscope slides is desirable, and in particular to where the arrangement of the cells within a sample is to be maintained or controlled.

Figure 1:
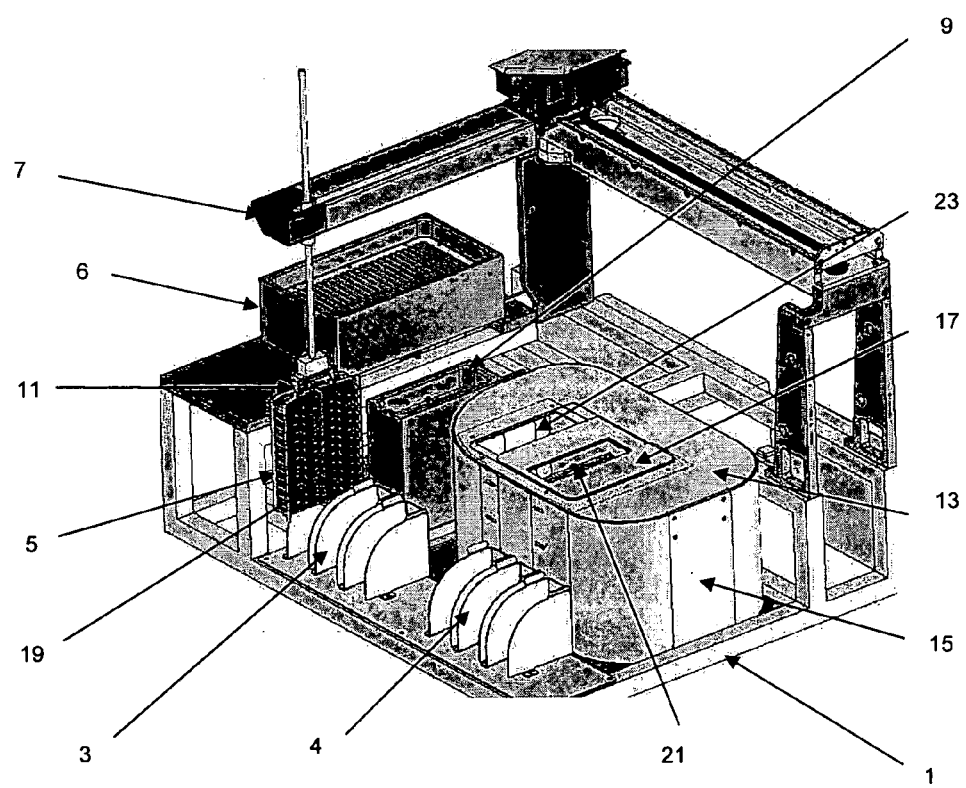
FIG. 1 shows an automated embedding device according to an embodiment of the present invention.
Figure 3:
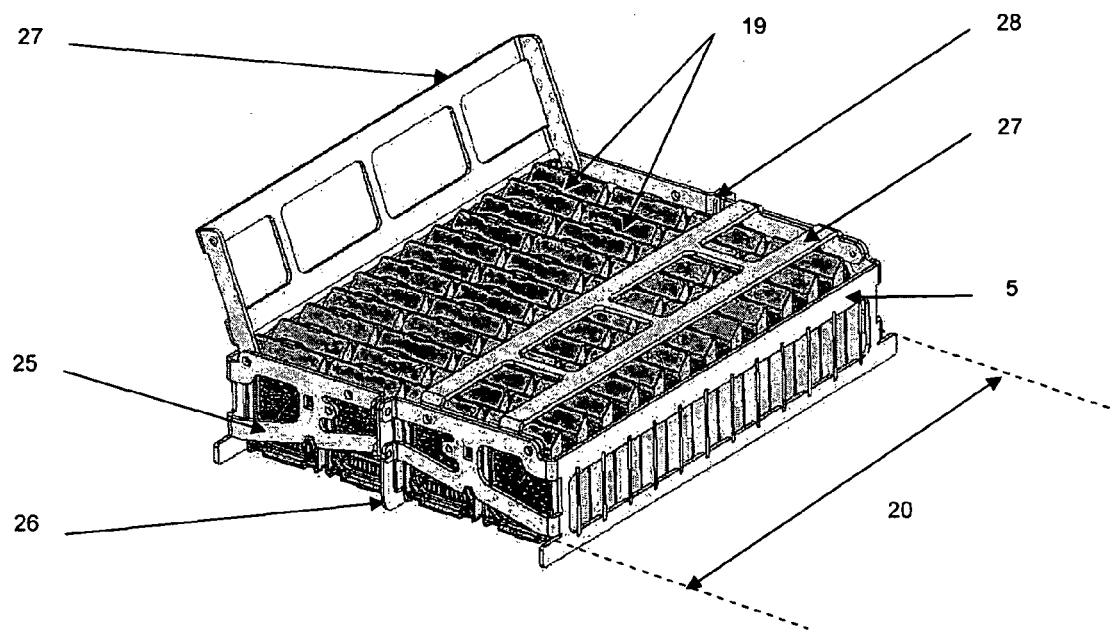
FIG. 3 shows an input member loaded with tissue supports according to an embodiment of the present invention.

Referring to FIG. 1, an automated embedding device 1 is provided comprising one or more input stations in the form of slots 3 and output stations in the form of slots 4 for receiving and/or storing one or more input members 5, an embodiment of which is shown in FIG. 3. The number of input slots 3 and output stations 4 provided may be modular and hold different numbers of input members depending upon the throughput requirements of the laboratory. Input and output stations provide for random access and continuous operation of device 1. For example a number of input members can be placed in the input slots and queued until ready for embedding, then stored in an output slot, providing the instrument with a continuous throughput of cassettes without human intervention. In the present embodiment, three input slots and three output slots are shown, however more or fewer may be provided. It is not necessary for the number of input slots to match the number of output slots.

Input slots 3 and output slots 4 may be provided with a sensor (not shown) to detect the presence of the input member 5 in the input slot 3 and output slot 4. This sensor may be remote from, or incorporated into, the input slot 3 and output slot 4, and may be in the form of an optical, mechanical, electronic, capacitative, inductive, magnetic, pressure etc switch that is activated when the further input members are in position in the input slot 3 or output slot 4, and deactivated when it is removed. In one embodiment, the sensor is an optical imaging system. Examples of sensors include, but are not limited to, an infra-red detector, RF waves, sonar, radar waves, X-rays, magnetic resonance, interferometers and optical scanning devices using, e.g., focused light beams or lasers. Other methods and devices for determining the detection of further input members 5 in the input slots 3 and output slots 4 may also be used.

Embedding device 1 includes a transfer assembly 7 for transporting input member 5 to embedding chamber 9. The transfer assembly 7 may be any form of transfer mechanism, and include such components as a gantry, lead screw, carousel, electromagnet, cam arrangement, a Selective Compliant Assembly Robot Arm (SCARA), multi-axis arm, Cartesian robot, an XY robot or Z theta robot suitable for transporting the input member 5 to a embedding chamber 9. In the present embodiment, the transfer assembly comprises an XYZ robot arm used to move input members from the input slots, to other areas of the device 1.

The transfer assembly 7 is provided with engaging means 11, such as a gripping mechanism for input member 5. In another embodiment, the engaging means is a hook which the transfer assembly positions under one end of input member, then moves vertically to engage the input member. In other embodiments, the engaging means may comprise a system of electro-magnets, a suction cup, and/or jaws actuated by a solenoid, a motor, hydraulics and/or pneumatics.

Figure 2:
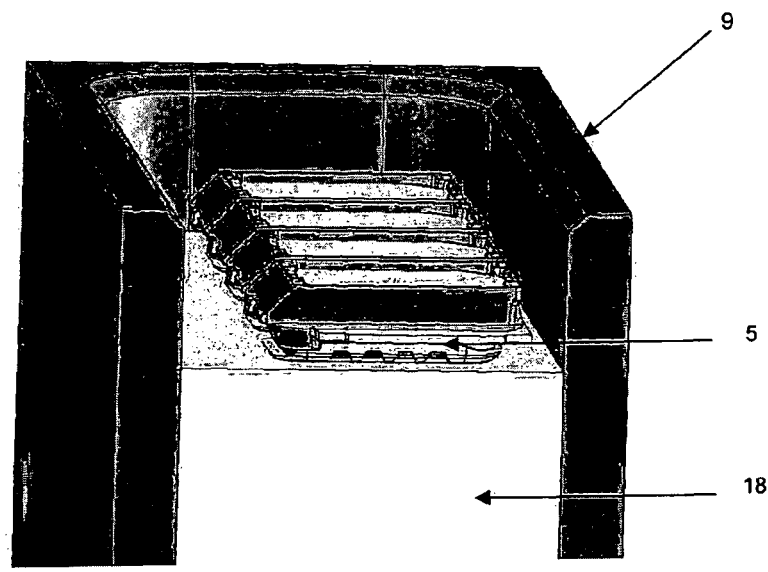
FIG. 2 is a cross-sectional view of an input member located within a reservoir filled with embedding media according to an embodiment of the present invention.

As shown in FIG. 1, an embedding chamber 9 is provided that may be integral with the embedding device 1 as shown in FIG. 1. Chamber 9 is configured to contain a volume of embedding media 18 and receive one or more input members 5 as shown in FIG. 2. The Chamber may be in fluid communication with a reservoir 6, which contains embedding material. In one form the embedding chamber may be in the form of a wax bath adapted to take one or more input members.

Any suitable embedding media may be used in accordance with the device 1. Paraffin is known and commonly-used as an embedding medium, however it will be appreciated that other embedding media, including but not limited to, TissueTek O.C.T., manufactured by Sakura Finetek ester, microcrystalline cellulose, bees wax, resins or polymers, such as methacrylates, may also be used as embedding media. Suitable resins and polymers, including Araldite 502 Kit, Eponate 12.™. Kit, and Glycol Methacrylate (GMA) Kit, are available from Ted Pella, Inc., Redding, Calif. Where a paraffin embedding material is used, the reservoir 6 and chamber 9 may employ heaters to melt the wax and/or keep the wax at an appropriate temperature. In one form the chamber 9 will have heaters to melt new wax placed into the reservoir 6.

In one embodiment, the embedding chamber 9 is provided with, or connected to, an ultrasonic device (not shown) or filtering system to, in operation, assist in cleaning the embedding media by removal of debris such as tissue debris, or other material which may affect the optimum operation of the embedding process. An agitator may also be provided in the embedding chamber to ensure that any solids or liquids are mixed.

In one embodiment, to cool the embedding media into a hardened block in the multiple tissue supports, the device 1 includes a cooling member such as a cooling chamber 13 comprising a cooling unit 15. Access to the cooling chamber 13 may be via automatic sliding doors 17 located at each end of the cooling chamber. Cooling chamber 13 may be configured to cool one or more input members 5 simultaneously. A number of different cooling members are possible.

In one embodiment (not shown), the input members may be left in a support so that ambient air surrounding the member cools the tissue supports and the embedding material held therein. Air may be forced past the tissue supports or natural circulation of air may be sufficient.

The forced air may be generated by a fan in an open environment, or the input member or tissue supports may be placed in a chamber 13. The chamber 13 may include a device for moving air past the tissue supports, and may also include a heat transfer mechanism to remove heat from the air moving past the tissue supports. Examples of heat transfer mechanisms include a cooled surface such as a heat exchanger, which itself may be cooled by liquid or airflow, or other means such as a Peltier device. In one form a finned surface having internal liquid pathways may be employed in an airflow in the chamber 13, such that air is pushed by a fan past tissue supports, then through the fins of the cooler. The liquid in the cooler takes heat away to for example a refrigeration unit, so that the air leaving the cooler is chilled, ready to recirculate through the fan and past the tissue supports again. The air may recirculate as described above, or fresh air may be drawn into the chamber, cooled through the cooler, moved past the tissue supports and expelled.

Other cooling methods may be used, such as baths of cooled liquid, or cooled liquid such as water sprayed into the air within the chamber to cool the air and increase the mass of cooling fluid passing through the chamber. When the embedding material is wax, water will not affect the tissue samples or embedding material.

The input member or tissue supports may be placed onto a cooling plate, such as a cooled metal plate, or may be placed into a cold liquid bath.

The cooling unit 13 includes a cooling mechanism, which may comprise an evaporator, compressor, condenser, expansion valve and/or an air mover such as a fan. In the aforementioned cases the coolant may be a gaseous fluid, such as air. Air may be pumped around the unit using a fan. Alternatively air from an external source may be used to provide a stream of air. If accelerated cooling is not required the input members may be left to cool in ambient air.

In other embodiments cooling may be conducted by a liquid such as water, or water sprayed into air to increase the cooling capacity of the air.

In operation, the cooling chamber 13 is in thermal communication with the input member 5 and multiple tissue supports 19, and is configured to dissipate heat from the embedding media. In one embodiment, the cooling mechanism comprises at least one fan which blows air across a fin or capillary containing a coolant and directs cooled air to the multiple tissue supports. The air need not be actively cooled and may be at ambient temperature, although cooled air will reduce the temperature more quickly.

In one embodiment, cooling chamber 13 includes a conveyor (not shown) for moving the input member 5 through the cooling chamber 13. For example, the cooling chamber 13 may be able to hold a number of input members for cooling. If only one input member is in the cooling chamber, then its position is not important, as it is the only object being cooled. However if another input member is added to the chamber then the air passing an input member will be heated. It is therefore advantageous to move the first input member to a first position, closer to the source of cooled air, and place the second input member, which will be hotter, after the first. In this way the first input member will cool at the maximum rate and be able to be withdrawn from the cooling chamber more quickly. A conveyor inside the cooling chamber may move the input members from a first position to a second position. Cooling of the embedding media typically takes from 3 to 20 minutes.

As a result of the above-described configuration, the embedded tissue samples are cooled by recirculating cold airflow, with heat being dissipated by air drawn from the upstream chamber 21. The tissue supports secured in the input member are cooled by air from the upstream chamber 21 moving through the downstream chamber 23, and most are cooled by being directly blown upon with air from the upstream chamber 21 by the at least one cooling fan (not shown).

The cooling unit could also comprise other means to assist in heat dissipation such as a heat sink preferably configured to dissipate heat from all the embedded tissue supports. In another embodiment, the cooling chamber 13 may be provided with an endless supply of liquid (e.g., a water line) and a liquid exhaust for disposing of heated liquid. In another embodiment, after removal from the chamber 9 by the transfer mechanism, the input member, in the form of a basket, may be placed into an intermediary stage for initial cooling, before entering the cooling chamber. The intermediary stage, termed a drip station, may include a fan for circulating air, and may be at ambient temperature, for example, between 20 degrees Celsius and 40 degrees Celsius. The intermediate stage may comprise a drip area, where any drips or excess wax is allowed to pool at the bottom of the basket. By not immediately cooling the basket, excess wax can be removed from the cassettes and basket before further cooling. In addition, it has been found to be advantageous to not cool wax too rapidly due to shrinkage of the wax, which can cause problems with obtaining the best quality embedding. By cooling with ambient air, the wax solidifies more slowly and can form a partial skin before more rapid cooling is performed. After a period of, for example, 4 minutes, the wax will have at least partially solidified. After initial solidification, the basket may be moved from the drip station to the cooling chamber 13, where additional cooling takes place. The cooling chamber 13 may be cooled as hereinbefore described, and be held at between 0 degrees and 14 degrees Celsius. In a more preferred embodiment, the cooling chamber may be held between 4 and 8 degrees Celsius. The basket may be held in the cooling chamber for a period of time until the wax in the cassettes reaches a desired temperature, for example below 12 degrees Celsius. This may take between 5 to 10 minutes depending on the initial temperature, amount of wax in the baskets, temperature of the cooling air and degree of circulation of air. It has been found that in particular, paraffin wax such as Paraplast wax commonly used in tissue processing and embedding, allows separation of the tissue cassette from mould, and separation from basket, better than higher temperatures.

After a predetermined period of time, the basket may be removed from the cooling chamber 13 to the output station. Alternatively, the basket may be kept in the cooling chamber until removed by an operator, or moved to a splitter as described herein. In another alternative the splitter may operate on the cassettes in the basket in the cooling chamber.

FIG. 16 shows a timeline of a typical instrument having a single transport mechanism in the form of a robot arm, and a plurality of baskets input sequentially. The robot arm is used to transport the baskets, and the time the robot arm engages the baskets is shown in grey. As there are times when the baskets are in a position for some time, such as the drip area and cooling chamber (described as chill in the figure) the robot arm is not needed to be in constant contact with the basket. This allows the baskets to be processed more than one at a time, as shown in FIG. 16.

In FIG. 3 the supports 19 are arranged in an array configuration. A tier-stacking dimension, which will be referred to as a longitudinal dimension 20 formed from a column of slides. The longitudinal dimension extends between two ends of the input member 5, a top end 26 and a bottom end 28. The tissue supports 19 may be arranged along the longitudinal dimension in a variety of arrangements, such as the staggered arrangements shown in FIGS. 11 and 12. Other arrangements are possible such as having the two arrays of supports in an input member. The Input member may also be cylindrical with tissue supports mounted in a circular array.

As shown in FIG. 3, input member 5 comprises a framework assembly 25 for holding a plurality of tissue supports 19 in a substantially tiered arrangement. In the shown embodiment, input member 5 is provided with a close fitting and rigid gate portion 27 to minimise lateral movement of the tissue supports 19 when in use during the embedding process. Gate portion 27 also allows considerable force to be applied to the back edge of input member.

In another embodiment (not shown) the tissue supports are located by a clip, which holds the support in place within the input member. During the processing and embedding of the tissue the tissue supports are not subject to significant external forces, and may therefore only require a moderate locating force.

Figure 4A:
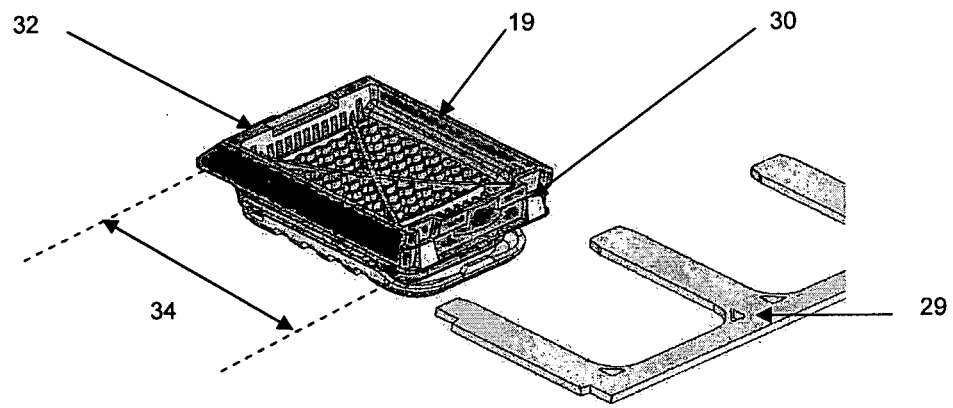
FIGS. 4A and 4B show an input member engaging a tissue support according to an embodiment of the present invention.
Figure 4B:
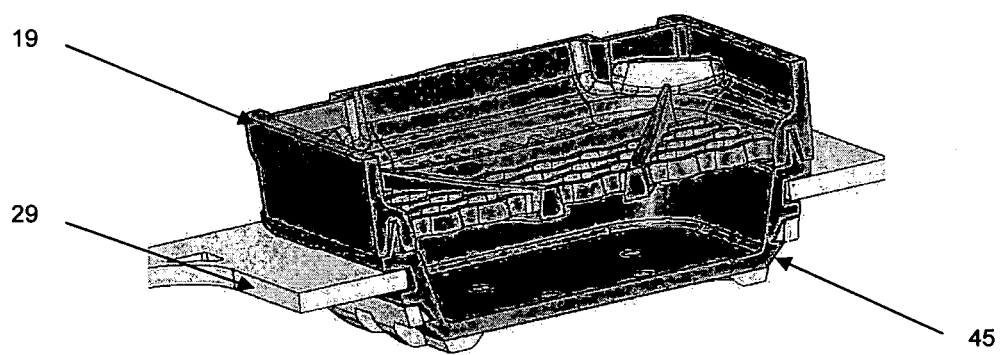
Figure 5:
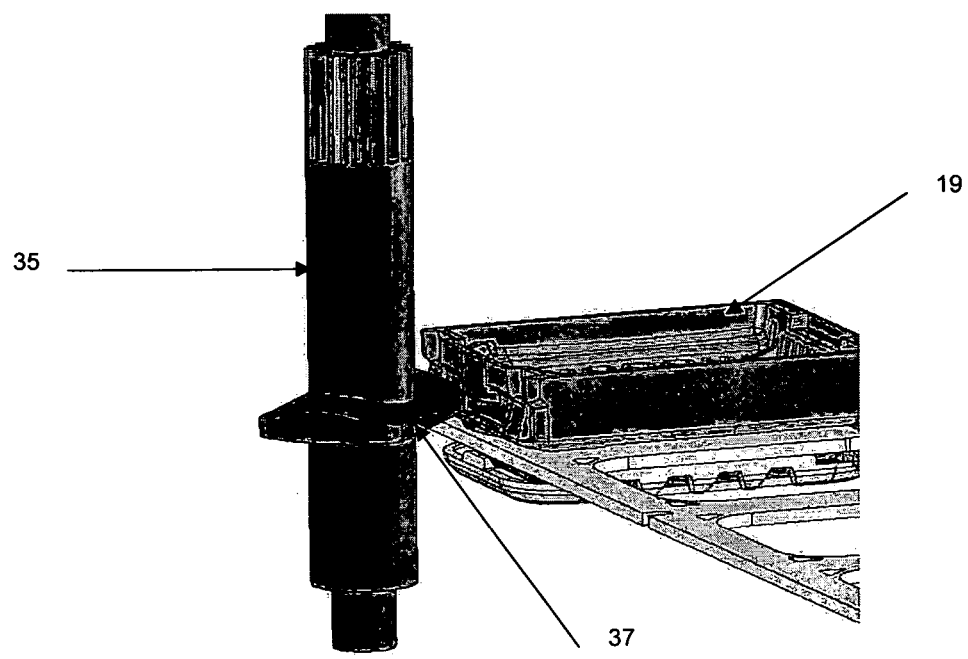
FIG. 5 shows a separating mechanism of the device according to an embodiment of the present invention.
Figure 6:
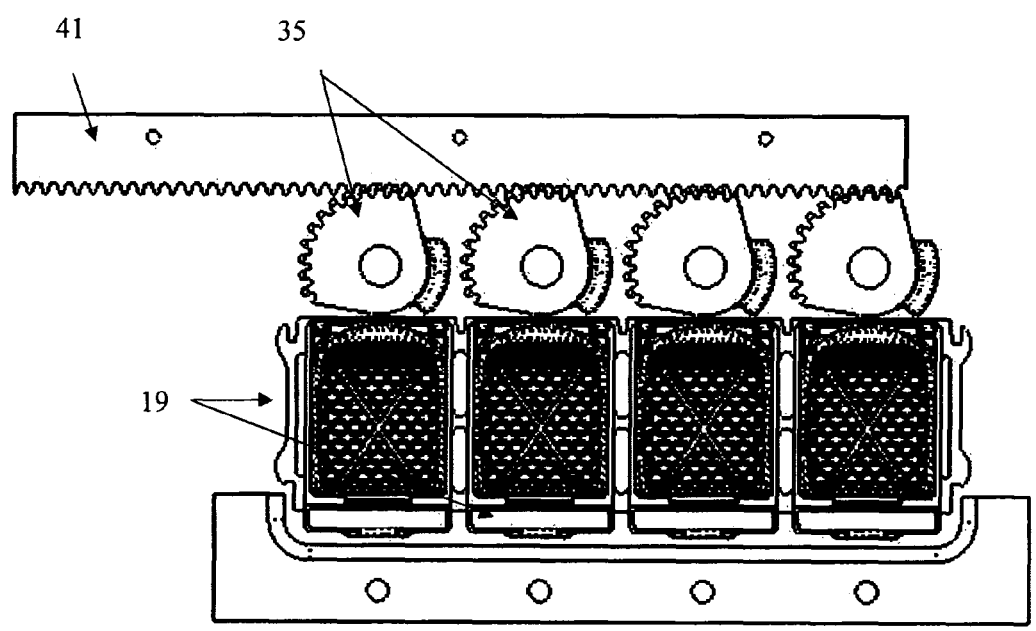
FIG. 6 shows a top view of a separating mechanism of the device according to an embodiment of the present invention.
Figure 7:
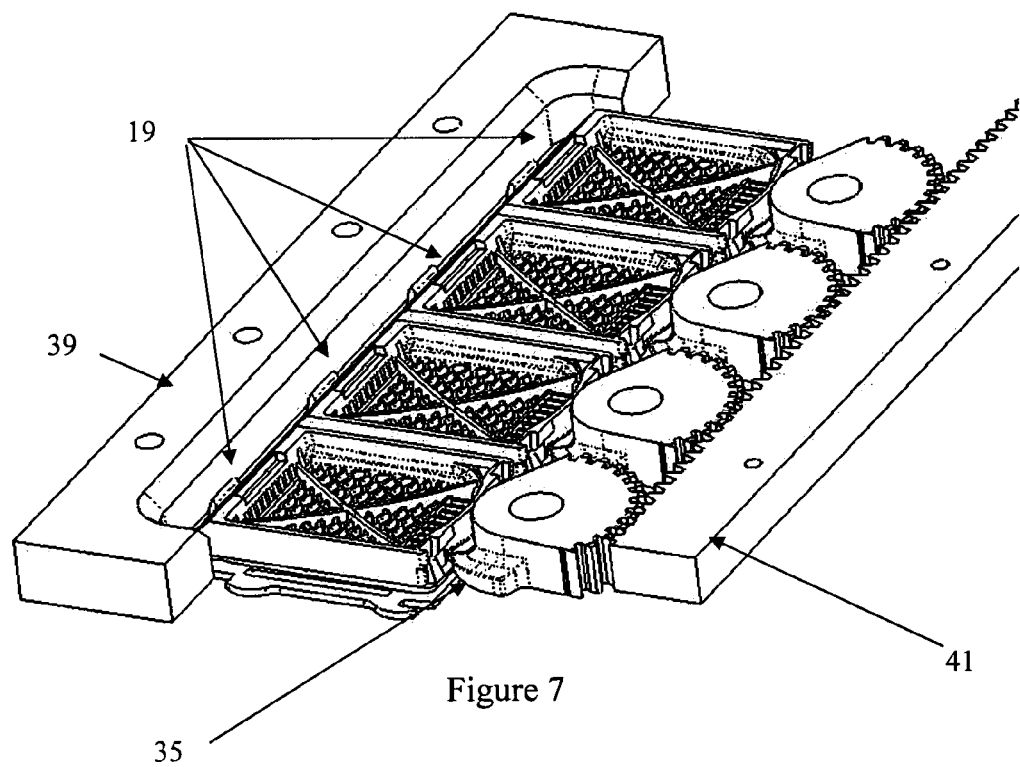
FIG. 7 shows a perspective view of a separating mechanism of the device according to an embodiment of the present invention.
Figure 8:
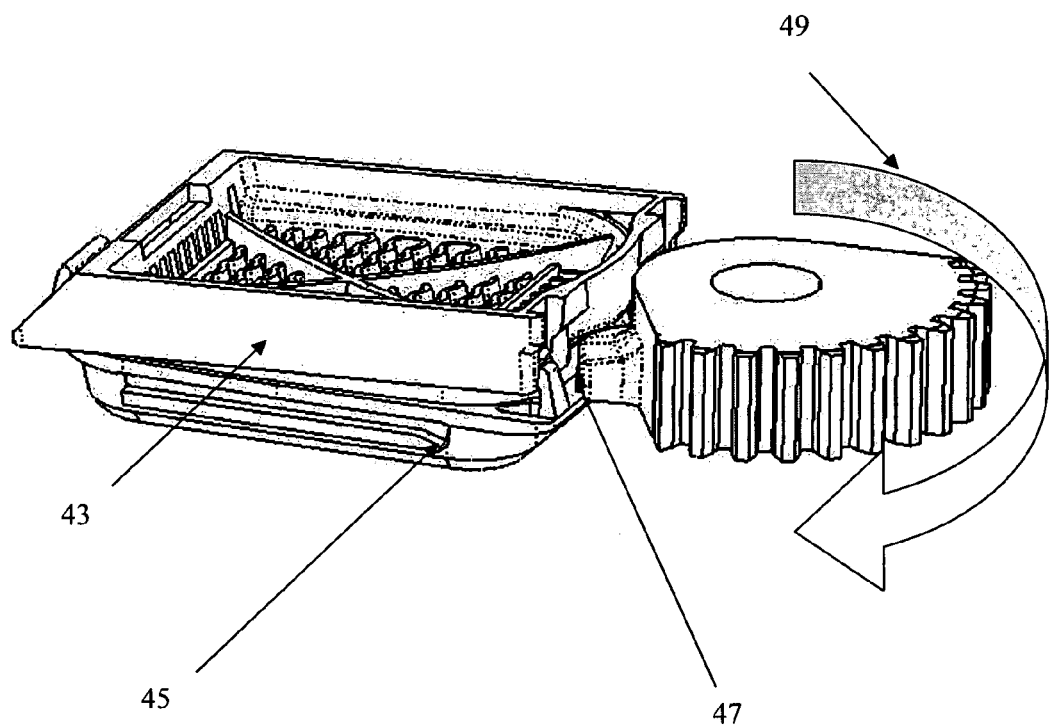
FIG. 8 shows the operation of a separating mechanism of the device according to an embodiment of the present invention.

As shown in FIG. 4B, in one embodiment input member 5 holds tissue support by the mould component 45 only, creating a gap between the underside of the tissue support 19 and the frame of the input member 5. The provision of a gap, in combination with tissue supports being positioned substantially vertically, allows reagents to easily drain away, minimising the amount of carry over of fluids. This arrangement also allows embedding media to drain when in use and reduces the need to scrape cooled embedding media off the blocks before inserting them into the microtome. Draining of the embedding media during operation of the device of the present invention also results in a consistent level of wax in the tissue support independent of tissue and tissue support size.

With reference to FIG. 4A, similar to the input member 5, each tissue support 19 has opposite longitudinal ends, a top end 30 and a bottom end 32, along (and with respect to) the longitudinal dimension 34. To engage tissue support, input member 5 has at least one gripping portion 29, as shown in FIGS. 4A and 4B.

Tissue supports of a variety of sizes can be inserted into the input member 5. In one embodiment, as shown in FIG. 3, the capacity of input member 5 is 48 tissue supports. Input member 5 may include an identifier, where the identifier may comprise features such as bar codes, RFID tags or OCR tags to allow the input member to be identified and transported by the device 1. The identification may be a unique identifier for each input member, or it may be a general identifier designating a type of processing or embedding to be performed. The identifier may be automatically identified by a reader that may be associated with an embedding station or tissue processor or other apparatus.

In one embodiment, the input member 5 is compatible with the retort of a tissue processor instrument, such as a Peloris™ rapid tissue processor or Tissue Tek VIP tissue processor. For example the input member may be adapted to fit within the confines of a tissue processor retort, and may be stackable so that more than one input member fits efficiently within the retort while still allowing efficient processing of the tissue samples held therein. Embedding may be achieved by applying an input member 5 directly from a tissue processor to the automated embedding device 1.

As shown in FIGS. 5, 6, 7 and 8, a separating mechanism is provided. In one form the separating mechanism comprises a cam 35 and drive rack 37. Separating mechanism comprises at least one cam 35 per row of tissue supports. Cam 35 comprises a lug 47. The separating mechanism may comprise a guide member 39 to facilitate separation of the lid portion 43 of the tissue support from the base mould 45. Other types of separating mechanism may be used which may be automated or manual.

In operation of the embedding device, the transfer assembly gathers the chilled input member and indexes it past the separating mechanism, wherein rack 41 drives the cam 35 in direction of rotation 49 wherein lug 47 engages a portion of the tissue support 19 and provide automated separation of components of the tissue support 19 to allow access to the embedded tissue block for further tissue handling. Lug 47 of cam 35 wedges loose the components of the tissue support 19, and breaks the adhesion between embedding material and mould while maintaining the partnership of the tissue support components, allowing the user to check that the tissue has indeed transferred to the wax block.

Figure 9:
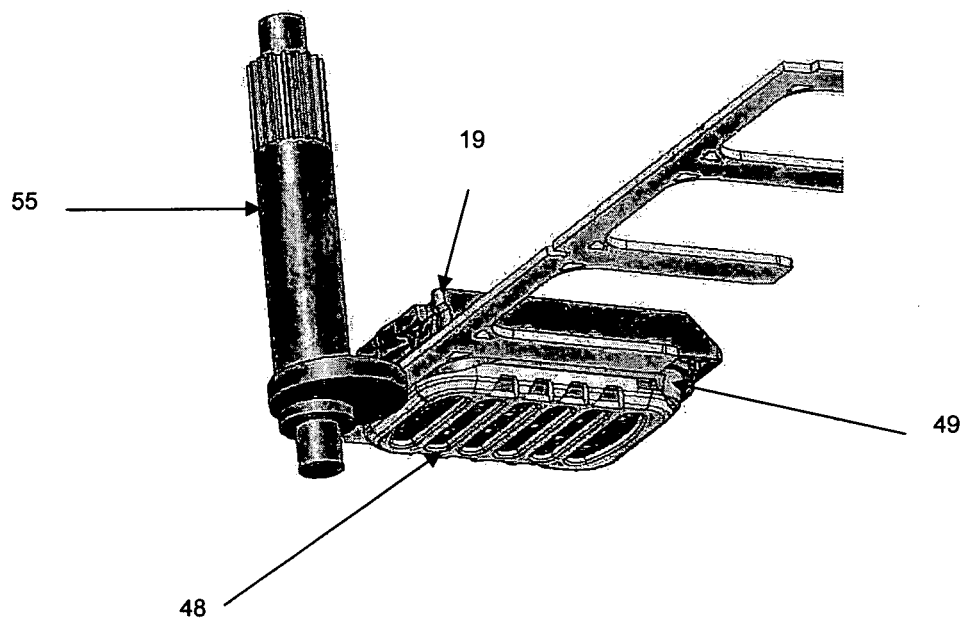
FIG. 9 shows a sealing portion of the device according to an embodiment of the present invention.

Some tissue supports may be provided with apertures to facilitate drainage of reagents during processing. A sealing portion may be provided in these tissue supports to seal the apertures and facilitate embedding as described in (incorporate by reference other embedding patent application). In one embodiment, as shown in FIG. 9, a sealing cam 45 is provided to engage and move the sealing portion 48 of the tissue support 19. In operation, the sealing cam 45 driven by a rack (not shown) and pinion engages and moves the sealing portion 48 relative to the mould 45 to seal apertures shown in FIG. 4b. The number of cams will be related to the number of columns of tissue supports. In one embodiment, a plurality of cams driven by a single rack and pinion is provided.

In one embodiment, device 1 is provided with a heating chamber or tray for heating the tissue samples prior to embedding. In one embodiment, the heating chamber comprises the condenser component of the cooling system. Other direct and indirect heating methods may be used. Preheating the tissue samples, which have already been infiltrated with wax before embedding, may shorten the time the tissue needs to be in the wax bath. Further, pre-heating the tissue may enable a better consistency between the wax in the tissue samples and the wax in the wax bath.

Figure 10:
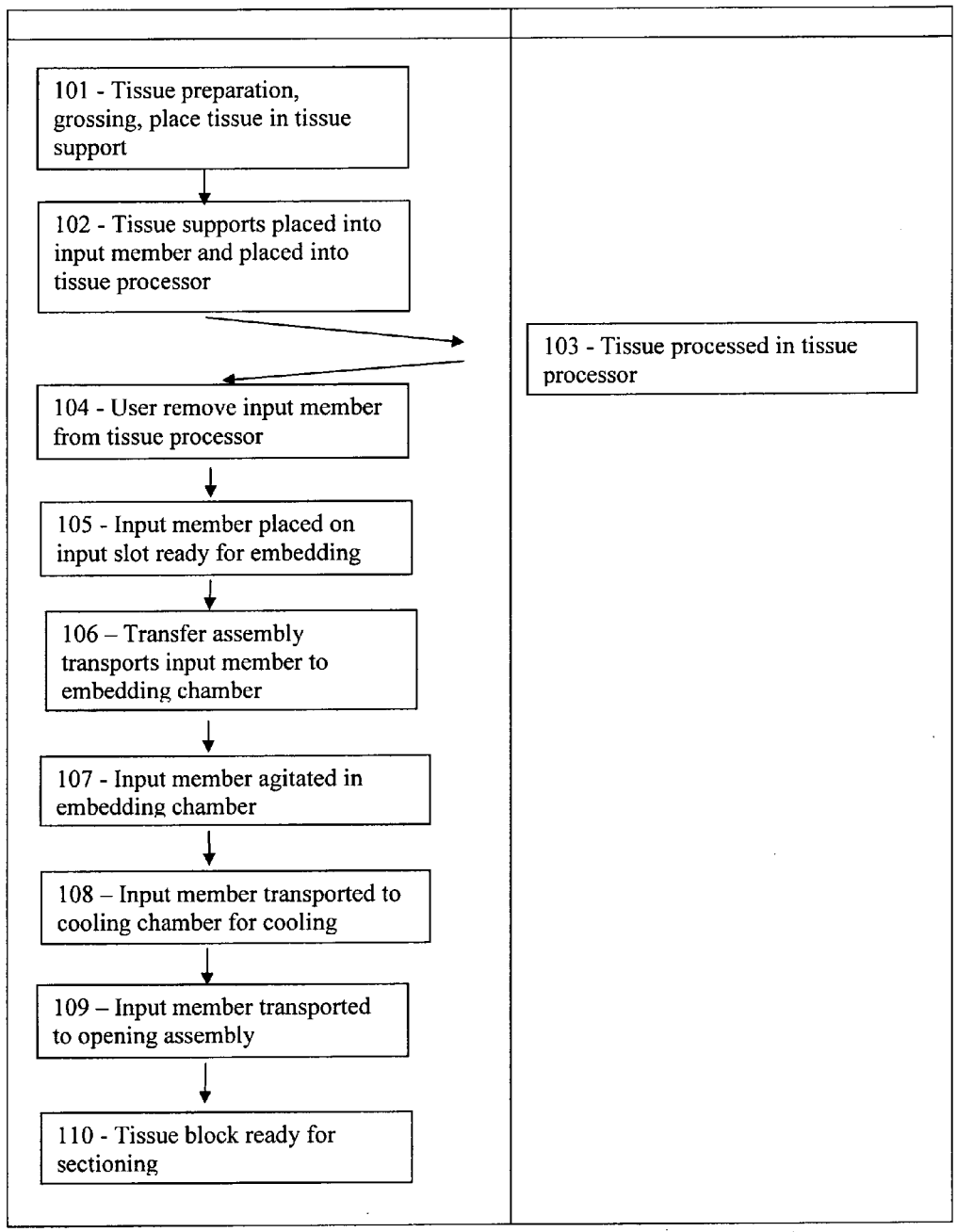
FIG. 10 shows a flowchart of a method according to an embodiment of the present invention.
Figure 11:
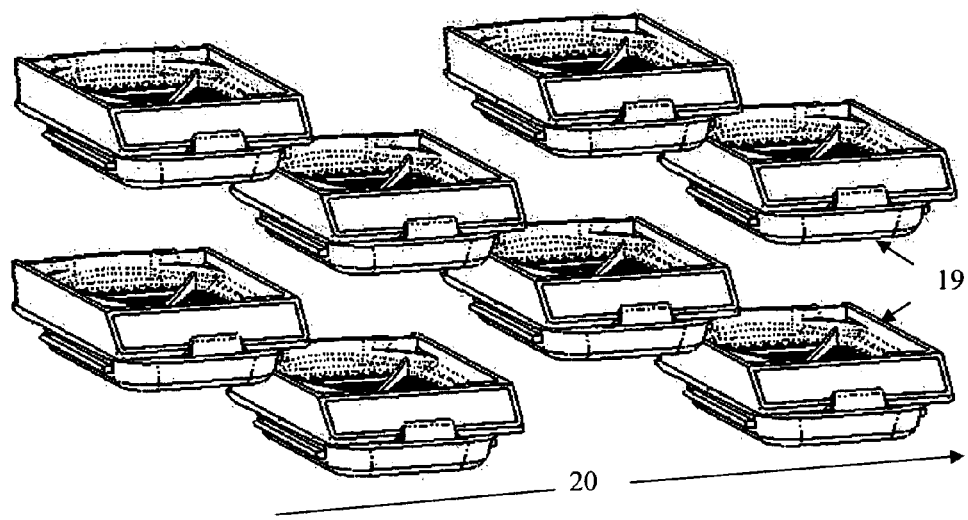
FIG. 11 shows a tiered arrangement of tissue supports according to an embodiment of the present invention.
Figure 12:
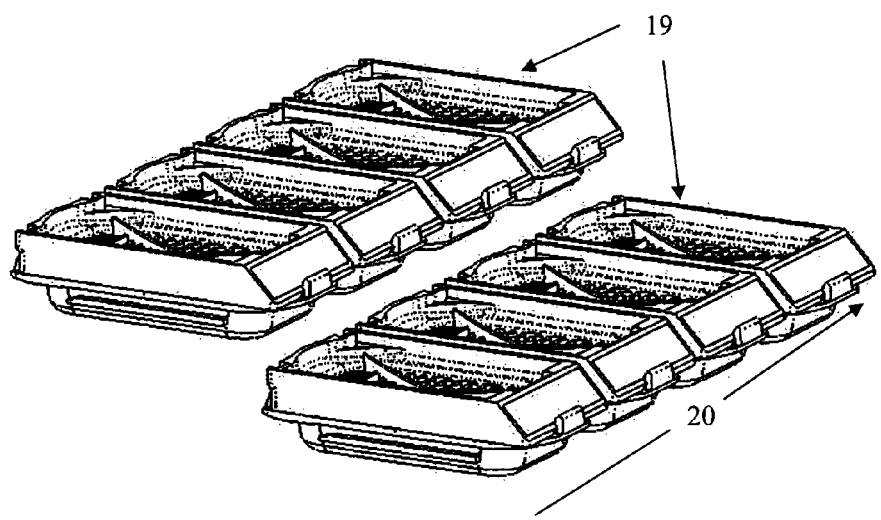
FIG. 12 shows a tiered arrangement of tissue supports according to an embodiment of the present invention.

FIG. 10 shows a flowchart of a method according to an embodiment of the present invention as related to a histology laboratory. First, in step 101 of FIG. 10, a tissue sample is placed in a tissue support, such as a cassette or mould. The tissue supports are then placed into an input member such as a basket or rack, and then placed into a tissue processor for processing at step 102. The tissue is processed at step 103 and removed from the processor at step 104. At step 105, the input member is loaded onto the input assembly of the automatic embedding device. In step 106, the input member is transferred to the embedding chamber. As described herein, the input member may be slowly entered into the embedding chamber at an angle to the vertical, to assist in removing pockets of air from the input member assembly of basket or frame, and multiple tissue cassettes in an array. Typically the input member is inserted slowly, for example, 5-10 mm/s, to allow time for the air to move away from the input member. Once fully inserted, the input member may be brought back to a vertical position, and held for several minutes to ensure that the embedding process completes successfully. A typical insertion time may be 2-5 minutes, preferably 3 minutes depending on embedding media, cassette design and other parameters. While the input member is immersed, it may be held by the transfer mechanism. In one embodiment, the transfer mechanism may shake or move the input member in the embedding chamber to assist in removing air bubbles and also to assist in promoting a flow of embedding material through the cassettes to ensure a more even heat transfer to the cassette and processed tissue samples. Alternatively, a mechanism inside the embedding chamber, such as in impeller or other fluid movement mechanism, may cause fluid flow internal to the embedding chamber to assist in removing bubbles and promoting even temperatures through the input member.

In step 108, the input member is transferred to the cooling chamber for cooling. As herein described this cooling may be done in a single chamber, which may have different cooling zones, or there may be two chambers, one comprising an ambient temperature drip area, and another chamber or region held at a chilled temperature. As the embedding chamber, when filled with wax, is typically around 65 degrees Celsius, ambient temperature (for example 20-40 degrees Celsius) will still allow the embedding material to cool, but at a slower rate than if chilled.

In step 109, the input member may optionally be transported to an opening assembly to allow the cassettes to be separate from the mould and/or basket within which they have been held.

In the present embodiment the tissue cassette is attached to the mould throughout the tissue processing.

The operation of the device 1 will now be described with reference to embodiments shown in FIGS. 1 to 12.

Transfer assembly 7 engages and transports input member 5 from input slot 3 into embedding chamber 9. Embedding chamber 9 may be pre-filled with embedding media, or the chamber 9 may be filled with embedding media from a wax bath reservoir 6 after insertion of the input member 5. Molten embedding media may be fed into the chamber 9 by a valve. Chamber 9 may be provided with a level sensor that senses when the level of embedding media reaches the top of the input member in the reservoir.

The temperature of the wax bath may vary according to user requirements, but is typically kept at a temperature above the melting point of the embedding media. A typical wax bath temperature would be 65° C. when paraffin wax is used as an embedding media.

The tissue in the tissue support is heated by the embedding material in the bath for a period of time, typically 1 to 10 minutes, to bring the tissue to the same temperature as the molten embedding media.

In use, the wax level will decrease as each input member 5 is drawn out of the chamber 9 and wax fills each mould. Where provided, a level sensor activates a valve connected to an elevated main embedding media bath reservoir and melter 6, and the chamber tops up under gravity when the level of embedding media decreases to a predefined level.

In another embodiment, the reservoir is filled and/or drained by use of pressure or a vacuum.

When apertures and sealing portions are provided on tissue supports, the apertures on each row of tissue supports are sealed in turn using cams 35 driven by a rack 41.

Input members 5 may be agitated by transfer assembly 7 for a predetermined period of time. Agitation of the input members reduces bubble formation in the finished blocks and decreases the heating time by providing a fluid flow through the input members 5. Other methods such as using surface acoustic waves (SAW), ultrasonics, vibration, sealing and pressurising the reservoir or sealing and applying a vacuum may be used. An impeller, stirrer or any agitator (not shown) may also be located within the chamber 9 to cause a flow of embedding media around the input member.

Additionally, the input member may be placed into the bath at an angle to the horizontal, or angled once in the bath, to assist in removing bubbles in the mould. To achieve such an angle, the transfer assembly may tilt the input member. Typically the input member may be tilted from 5 to 30 degrees from the vertical. In a more preferred form, the input member is tilted between 10 and 20 degrees from vertical. In an even more preferred embodiment, the input member is tilted 15 degrees from vertical. When removed in the present embodiment, it is preferable that the tissue supports and mould are substantially horizontal so as to provide a consistent level of wax fill and ensure the correct amount of wax is used.

After a predetermined time, typically 1 to 10 minutes, the input member 5 is drawn slowly out of the chamber 9, scooping up embedding media in the tissue supports at the same time. Slow withdrawal of the input member 5, such as a velocity of between 5-10 mm/s, typically results in a cleaner rack as embedding media wicks down the input member 5 during withdrawal from the chamber 9. As the input member 5 and tissue support 19 will be at the same temperature as the embedding media, they will be resistant to the build-up of embedding media.

In one embodiment, the transfer assembly 7 places the basket on a heated surface to wick away any remaining wax droplets from the bottom of the input member before it has time to solidify. During this time, the wax in the cassettes will still cool from its elevated temperature, but at a slower rate than if it was in a cooling chamber.

After filling with embedding media, the transfer assembly 7 transports the input member 5 from the chamber 9 to the cooling chamber 13. Cooling chamber is typically maintained at a temperature of from 0° C. to 15° C. The sliding door 17 on cooling chamber 13 opens and the input member 5 is inserted into the downstream chamber 23. Where provided, a conveyor (not shown), such as an overhead conveyor, transports the input member through a flow of chilled air in the cooling chamber 13 to the upstream chamber 21. Cooling of the embedding media typically takes from 5 to 15 minutes. Multiple input members may be chilled simultaneously.

The transfer assembly then returns to the input slot 3 to commence the process again by transporting a further input member 5 to the chamber 9 while the first input member is cooling.

At the upstream chamber, the transfer assembly gathers the chilled input member 5 and indexes it past a separating mechanism. In one embodiment, the separating mechanism comprises cams 35 having lugs 47 which wedge the cassette and wax block loose from the mould 45.

The input member 5 is then transported to an available output slot 4 by the transfer assembly 7.

In one form a detachment mechanism is provided to move the mould 45 relative to the input member 5. After embedding, excess wax typically binds the mould and tissue support to the frame of the input member. A mechanism as described above may be used to separate the mould from the tissue support after embedding, but at this point the mould 45 may still be bound to the frame of the input member due to hardened wax left over from embedding. The detachment mechanism may be engaged prior to, during or after separating the mould from the tissue support, and moves one or more moulds relative to the input member. The movement between the mould and input member may be small, for example merely sufficient to break any wax connection between the two parts. This will make removal of the mould and the tissue support from the input member much easier for a human operator. The detachment mechanism may also move the mould partially or completely from the input member.

Figure 13:
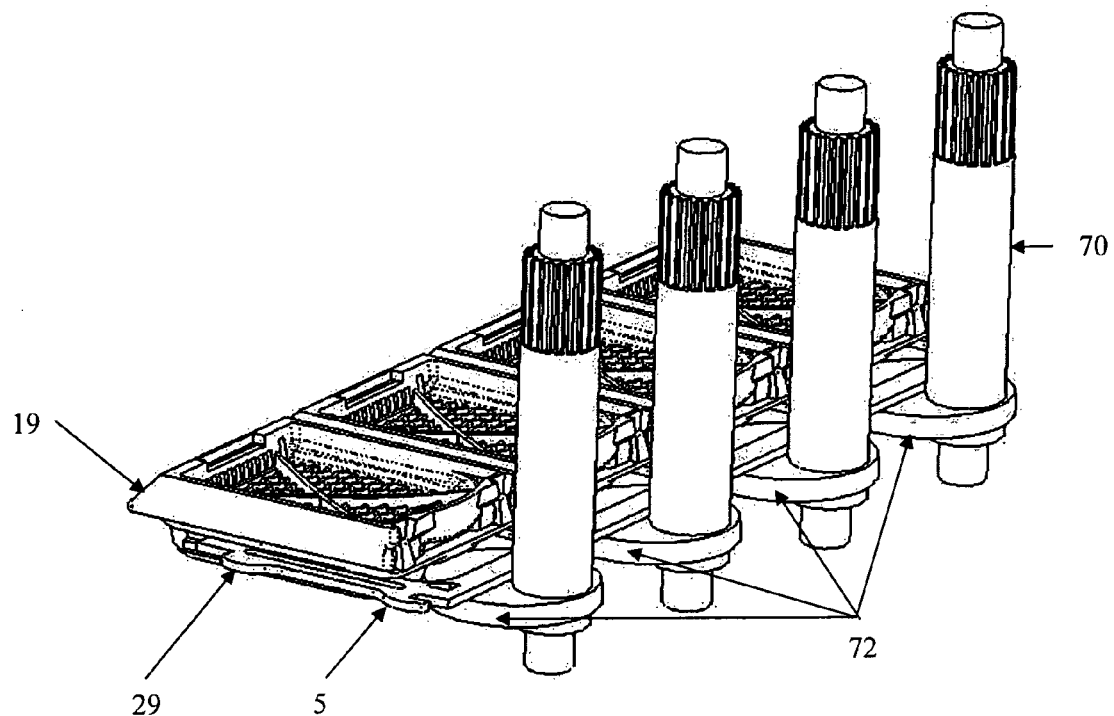
FIG. 13 shows a perspective view of a detachment mechanism of the present invention.
Figure 14:
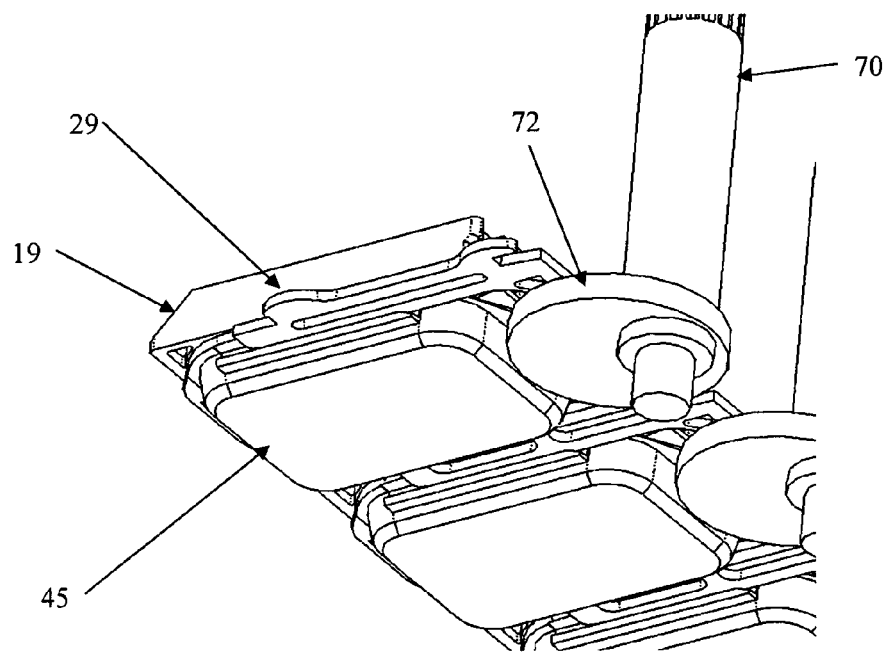
FIG. 14 shows a perspective view of a portion of the detachment mechanism shown in FIG. 13.
Figure 15:
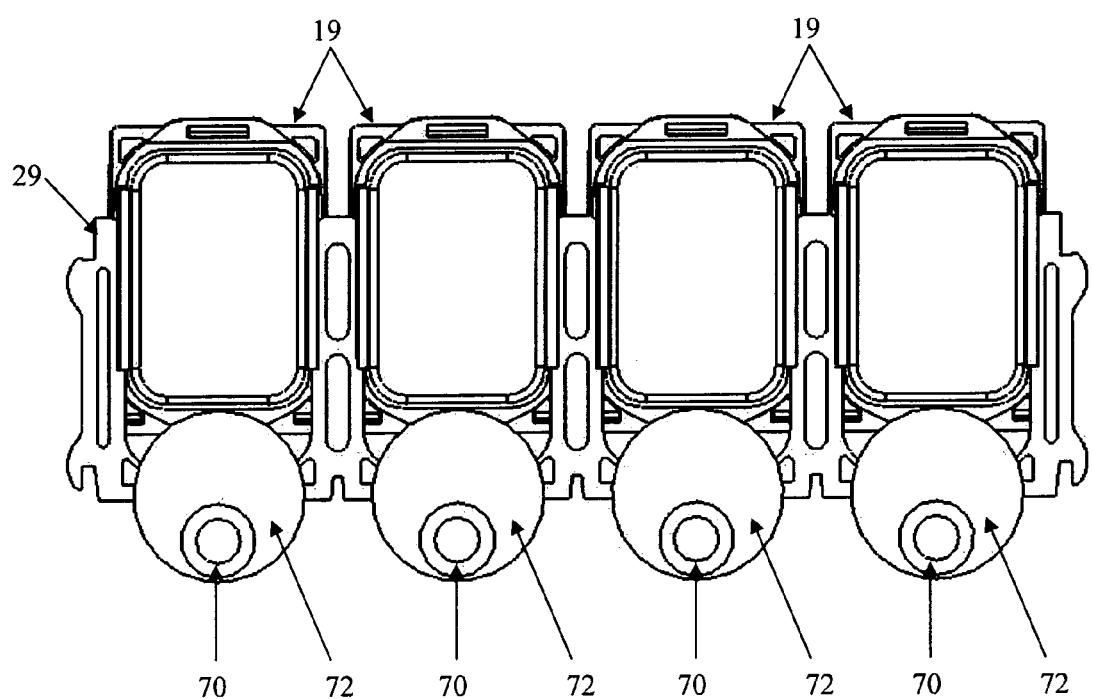
FIG. 15 shows a plan view of the detachment mechanism of FIG. 13.

An example of a mechanism that forms part of the separator is shown in FIGS. 13, 14 and 15. In these figures only one row of tissue supports in an input member is shown, however the mechanism may act on more than one row at once, and/or may move between rows.

In FIG. 13 a number of shafts 70 are provided, each with a cam 72. A cam 72 may engage with a mould 45, and as the shaft 70 turns, the cam 72 pushes the mould 45 out of the gripping portion 29 of the input member 5. The degree of movement may be controlled by the amount of rotation of the shaft and/or the size of the cam. In FIG. 13, a shaft is shown for each of the moulds. Each shaft may have one or more cams. In FIG. 13 only a single cam is shown, however, there may be multiple cams distributed along the shaft, for example, one cam for every row of gripping portions in the input member. Further, in FIG. 13, a shaft and cam is provided for each mould, however in another embodiment, the shaft may move along the row and disengage a mould one at a time.

In FIG. 14 a close-up of the contact between the cam 72 and the mould 45 is shown. As the cam 72 turns, the mould is pushed from the input member. Tissue support 19 is shown associated with the mould 45, and it may be that the tissue support has previously been separated from the mould, but the wax block attached to the tissue support may lie in the mould 45.

In FIGS. 13, 14 and 15, no retaining mechanism is shown for the moulds. When separating the mould from the input member, a retaining mechanism such as gate 27 would be disengaged. Other retaining mechanisms such as a clip (not shown) may releasably hold the moulds in place, or alternatively the gripping portions 29 may employ a slight interference fit to hold the mould in place. Projections on the end of the gripping portion 29 may also provide a click-type retaining mechanism to prevent the mould from falling out of the input member 5 without requiring gates, but enabling the moulds to be released upon sufficient force being applied to the moulds form for example the cam 72 of the detachment mechanism.

Other detachment mechanisms are possible, for example the input member could be held firmly in place and an arm may move towards the input member to be in contact with one or more of the moulds, to detach a single mould, a row of moulds or all moulds at once. The detachment mechanism may be a separate device or integral to the automated embedding device of FIG. 1.

If the detachment of the mould is to take place before the tissue support and mould are separated then the detachment mechanism may engage with the tissue support rather than the mould. In another embodiment the detachment mechanism may engage both the tissue support and the mould.

Operation of the device according to the present invention provides for continuous throughput of tissue supports for example wherein one input member is cooling in the cooling chamber and another input member may be located in the reservoir, and further input members located in the input and output slots. The arrangement of the present device provides for embedding of typically 1-100 tissue supports per batch.

While the invention has been described in connection with preferred embodiments and examples, it will be understood by those skilled in the art that other variations and modifications of the preferred embodiments described above may be made without departing from the scope of the invention. Other embodiments will be apparent to those skilled in the art from a consideration of the specification or practice of the invention disclosed herein. It is intended that the specification is considered as exemplary only, with the true scope and spirit of the invention being indicated by the following claims.

"Comprises/comprising" when used in this specification is taken to specify the presence of stated features, integers, steps or components but does not preclude the presence or addition of one or more other features, integers, steps, components or groups thereof."

The invention claimed is:

1. A tissue embedder comprising:
   a transport mechanism for at least two input members, each input member adapted to hold a plurality of tissue supports, with each tissue support associated with a mould;
   a wax bath configured to receive into the wax bath a first input member holding the plurality of tissue supports; and
   a cooling chamber configured to receive the first input member in the cooling chamber;
   wherein the transport mechanism is configured to move the first input member holding the plurality of tissue supports from the wax bath to the cooling chamber,
   wherein the transport mechanism is configured to transport a second input member into the wax bath while the first input member is in the cooling chamber.

2. The tissue embedder of claim 1 further comprising a wax removal station, for removing excess wax from the tissue supports prior to cooling.

3. A tissue embedder comprising:
   at least two input members, each configured to hold a plurality of tissue supports; at least two input slots, each slot configured to receive an input member;
   an embedding chamber sized and shaped to receive embedding media as well as a first input member holding a plurality of tissue supports, wherein a heater is associated with the embedding chamber to heat the embedding material,
   a cooling chamber sized and shaped to receive a first input member, wherein a cooling unit is associated with the cooling chamber to cool the embedding material,
   a transfer assembly configured to move the first input member between a first input slot, the embedding chamber, and the cooling chamber,
   wherein the transfer assembly is configured to move a second input member from a second input slot to the embedding chamber while the first input member is in the cooling chamber.

4. The tissue embedder of claim 3, wherein the embedding chamber has a top opening.

5. The tissue embedder of claim 4, wherein the transfer assembly can lower the input member into embedding chamber through the top opening either vertically or at an angle from vertical.

6. The tissue embedder of claim 5, wherein the angle is between 5 and 30 degrees.

7. The tissue embedder of claim 3, wherein the input member is configured to hold the plurality of tissue supports in a substantially tiered arrangement.

8. The tissue embedder of claim 7, wherein input member holds each tissue support in the plurality horizontally.

9. The tissue embedder of claim 3, wherein each tissue support comprises a tissue cassette and a mould.

10. The tissue embedder of claim 3, further comprising a separating mechanism for separating each tissue support from the input member.

11. The tissue embedder of claim 3, further comprising a wax removal station.

12. The tissue embedder of claim 1, wherein the cooling chamber solidifies the wax in each mould, such that the input member may be moved without disrupting or losing the wax.

* * * * *